US00PP35355P2

(12) United States Plant Patent
van Sambeek

(10) Patent No.: US PP35,355 P2
(45) Date of Patent: Aug. 29, 2023

(54) ***PHLOX* PLANT NAMED 'DOPHLEARBLUPOP'**

(50) Latin Name: *Phlox paniculata*
Varietal Denomination: Dophlearblupop

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/991,591

(22) Filed: Nov. 21, 2022

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phlox* plant named 'Dophlearblupop', characterized by its upright and uniform plant habit; vigorous growth habit and moderate growth rate; freely branching habit; early and freely flowering habit; large white to light pink-colored flowers with reddish purple-colored centers; and good container and garden performance.

2 Drawing Sheets

Figure 1:
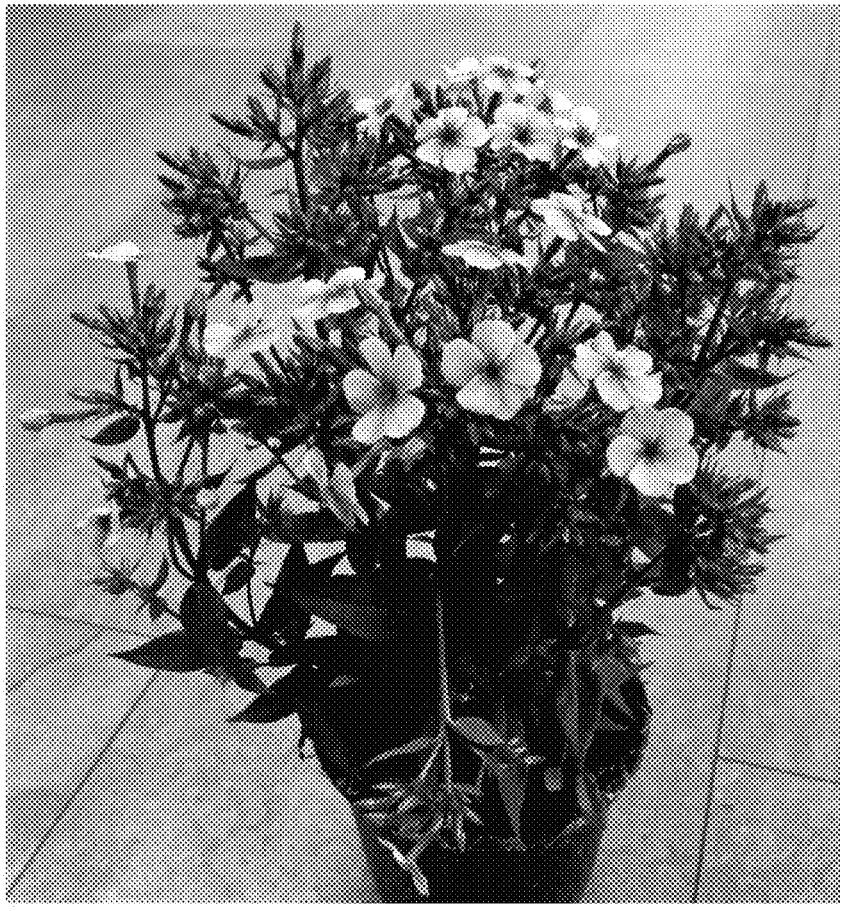

Botanical designation: *Phlox paniculata.*
Cultivar denomination: 'DOPHLEARBLUPOP'.

CROSS-REFERENCED TO CLOSELY-RELATED APPLICATION

An European Community Plant Breeder's Rights application for the instant plant was filed by the Applicant/Assignee, Dümmen Group B.V. of De Lier, The Netherlands on Aug. 15, 2022, application number 2022/1928. Foreign priority is not claimed to this application.

BACKGROUND OF THE INVENTION

The present invention relates to a new and distinct cultivar of *Phlox* plant, botanically known as *Phlox paniculata* and hereinafter referred to by the name 'Dophlearblupop'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from an open-pollination in July, 2015 of a proprietary selection of *Phlox paniculata* identified as code number PA12-000223-001, not patented, as the female, or seed, parent with an unknown selection of *Phlox paniculata* as the male, or pollen, parent. The new *Phlox* plant was discovered and selected by the Inventor as a single flowering plant within the progeny of the stated open-pollination in a controlled environment in Aalsmeer, The Netherlands in July, 2016.

Asexual reproduction of the new *Phlox* plant by vegetative cuttings in a controlled environment in Aalsmeer, The Netherlands since August, 2016 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlearblupop'. These characteristics in combination distinguish 'Dophlearblupop' as a new and distinct *Phlox* plant:

1. Upright and uniform plant habit.
2. Vigorous growth habit and moderate growth rate.
3. Freely branching habit.
4. Early and freely flowering habit.
5. Large white to light pink-colored flowers with reddish purple-colored centers.
6. Good container and garden performance.

Plants of the new *Phlox* differ from plants of the female parent selection primarily in flower color as plants of the new *Phlox* have white to light pink-colored flowers with reddish purple-colored centers whereas plants of the female parent selection have solid pink-colored flowers.

Plants of the new *Phlox* can be compared to plants of *Phlox paniculata* 'Sweet Summer Ocean', not patented. In side-by-side comparisons, plants of the new *Phlox* and 'Sweet Summer Ocean' differ in the following characteristics:

1. Plants of the new *Phlox* flower earlier than plants of 'Sweet Summer Ocean'.
2. Plants of the new *Phlox* have smaller flowers than plants of 'Sweet Summer Ocean'.

3. Plants of the new *Phlox* have white to light pink-colored flowers with reddish purple-colored centers whereas plants of 'Sweet Summer Ocean' have bluish purple-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet (FIG. 1) is a side perspective view of typical flowering plant of 'Dophlearblupop' grown in a container.

Figure 2:
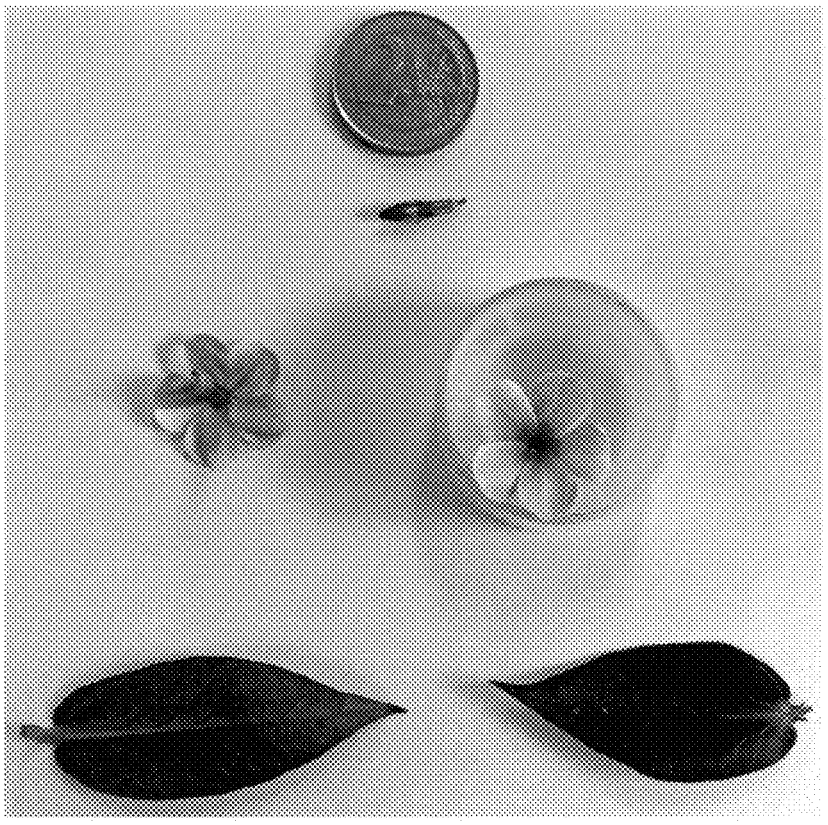

The photograph on the second sheet (FIG. 2) are close-up views of typical leaves, flower buds and flowers of 'Dophlearblupop'.

DETAILED BOTANICAL DESCRIPTION

The aforementioned photographs and following observations, measurements and values describe plants grown during the late spring and early summer in 13-cm containers in an outdoor nursery in Straelen, Germany and under cultural practices typical of commercial *Phlox* production. During the production of the plants, day temperatures averaged 21° C. and night temperatures averaged 15° C. Plants were pinched one time one week after planting rooted young plants and were 16 weeks old when the photographs and the description were taken. In the following description, color references are made to The Royal Horticultural Society Colour Chart, Fifth Edition, except where general terms of ordinary dictionary significance are used.

Botanical classification: *Phlox paniculata* 'Dophlearblupop'.

Parentage:

*Female, or seed, parent*.—Proprietary selection of *Phlox paniculata* identified as code number PA12-000223-001, not patented.

*Male, or pollen, parent*.—Unknown selection of *Phlox paniculata*, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and uniform plant habit; vigorous growth habit and moderate growth rate.

*Plant height*.—About 26 cm.

*Plant width* (*spread*).—About 27 cm.

*Lateral branches*.—Branching habit: Relatively freely branching habit; about four to five primary branches each with about 14 secondary branches developing per plant. Length: About 23 cm. Diameter: About 4 mm. Internode length: About 2.5 cm. Strength: Strong. Aspect: Upright to about 45° from vertical. Texture and luster: Smooth, glabrous; glossy. Color, developing and developed: Close to 143A; at the internodes, close to 187A.

Leaf description:

*Arrangement*.—Opposite, simple; decussate.

*Length*.—About 6.4 cm.

*Width*.—About 2.6 cm.

*Shape*.—Lanceolate.

*Apex*.—Acuminate.

*Base*.—Obtuse.

*Margin*.—Entire.

*Texture and luster, upper and lower surfaces*.—Smooth, glabrous; semi-glossy.

*Venation pattern*.—Pinnate, reticulate.

*Color*.—Developing and fully expanded leaves, upper surface: Close to N137A; venation, close to N137A. Developing and fully expanded leaves, lower surface: Close to 137D; venation, close to 137A.

*Petioles*.—Length: About 1 mm. Diameter: About 4 mm. Strength: Moderately strong; flexible. Texture and luster, upper and lower surfaces: Smooth, glabrous; semi-glossy. Color, upper surface: Close to 138A. Color, lower surface: Close to 137D.

Flower description:

*Flower type and flowering habit*.—Single rotate and salverform flowers arranged in compound terminal and lateral panicles; flowers face mostly upright to slightly outwardly depending on position on inflorescence; freely flowering habit with about 46 flowers per inflorescence and about 650 flowers developing per plant during the flowering season.

*Fragrance*.—Slightly fragrant; sweet, pleasant.

*Natural flowering season*.—Early flowering habit; plants begin flowering about twelve weeks after planting; plants flower in July in the garden in Germany and The Netherlands; flowers persistent.

*Flower buds*.—Height: About 1 cm. Diameter: About 3 mm. Shape: Conical. Texture and luster: Smooth, glabrous; matte. Color: Close to 72A.

*Inflorescence height*.—About 10 cm.

*Inflorescence diameter*.—About 14 cm.

*Flower diameter*.—About 2.2 cm.

*Flower depth*.—About 1.8 cm.

*Flower throat diameter*.—About 3 mm.

*Flower tube length*.—About 1.6 cm.

*Flower diameter, proximally*.—About 3 mm.

*Petals*.—Quantity per flower: Typically five in a single whorl; petals fused at the base into a narrow tube. Lobe length: About 1.1 cm. Lobe width: About 1.1 cm. Lobe shape: Obovate. Lobe apex: Rounded. Lobe margin: Entire, not undulate. Lobe texture and luster, upper and lower surfaces: Smooth, glabrous; matte. Throat texture and luster: Smooth, glabrous; matte. Tube texture and luster: Pubescent; matte. Color: Lobe, when opening, upper surface: Close to N155B; towards the throat, close to 77A. Lobe, when opening, lower surface: Close to N155B; random sectors, close to 77B. Lobe, fully opened, upper surface: Close to N155B and 75D; towards the throat, close to N74A; venation, similar to lamina colors; colors do not change with subsequent development. Lobe, fully opened, lower surface: Close to N155B; random sectors, close to 77B; venation, similar to lamina colors; colors do not change with subsequent development. Throat: Close to N74A; venation, close to N74A. Tube: Close to 77A; venation, close to 77A.

*Sepals*.—Quantity per flower: Typically five in a single whorl, fused towards the base; calyx, tubular. Length: About 9 mm. Width: About 1 mm. Shape: Subulate. Apex: Acuminate. Margin: Entire. Texture and luster, upper surface: Smooth, glabrous; matte. Texture and luster, lower surface: Smooth, glabrous; semi- glossy. Color: When opening, upper surface: Close to 144A variably tinged with close to N77A. When opening, lower surface: Close to 144A. Fully opened, upper and lower surfaces: Close to 144A variably tinged with close to N77A.

*Peduncles*.—Length: About 5 mm. Diameter: About 2 mm. Strength: Moderately strong. Aspect: About 45° from lateral branch axis. Texture and luster: Smooth, glabrous; glossy. Color: Close to 143A variably tinged with close to 187A.

*Pedicels*.—Length: About 3 mm. Diameter: About 1 mm. Strength: Weak. Aspect: Erect to about 45° from peduncle axis. Texture and luster: Smooth, glabrous; glossy. Color: Close to 143A variably tinged with close to 187A.

*Reproductive organs*.—Stamens: Quantity per flower: Typically five. Filament length: About 1 mm. Filament color: Close to 145C. Anther size: About 0.5 mm by 1 mm. Anther color: Close to 164B. Pollen amount: None observed. Pistils: Quantity per flower: One. Pistil length: About 1.8 cm. Stigma diameter: About 1 mm. Stigma shape: Three-parted. Stigma color: Close to 145B. Style length: About 1.6 cm. Style color: Close to 77A. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from about −30° C. to about 30° C. and to be suitable for USDA Hardiness Zones 3 through 9.

Pathogen & pest resistance: To date, plants of the new *Phlox* have not been observed to be resistant to pathogens and pests common to *Phlox* plants.

It is claimed:

1. A new and distinct *Phlox* plant named 'Dophlearblupop' as illustrated and described.

* * * * *